United States Patent
Chen et al.

(10) Patent No.: US 10,557,798 B2
(45) Date of Patent: Feb. 11, 2020

(54) SUBSTRATE SUPPORTED SEL STAGE AND HOUSING

(71) Applicant: Hewlett-Packard Development Company, L.P., Houston, TX (US)

(72) Inventors: Chien-Hua Chen, Corvallis, OR (US); Michael W. Cumbie, Corvallis, OR (US); Devin A. Mourey, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 16/098,096

(22) PCT Filed: Jul. 22, 2016

(86) PCT No.: PCT/US2016/043556
§ 371 (c)(1),
(2) Date: Oct. 31, 2018

(87) PCT Pub. No.: WO2018/017123
PCT Pub. Date: Jan. 25, 2018

(65) Prior Publication Data
US 2019/0145898 A1    May 16, 2019

(51) Int. Cl.
*G01J 3/44*    (2006.01)
*G01N 21/65*    (2006.01)

(52) U.S. Cl.
CPC ............. *G01N 21/658* (2013.01); *G01J 3/44* (2013.01); *G01N 2021/651* (2013.01)

(58) Field of Classification Search
CPC ... G01J 3/44; G01J 3/45; G01N 21/64; G01N 21/65; G01N 2021/651; G01N 21/00; G01N 21/43
See application file for complete search history.

(56) References Cited

U.S. PATENT DOCUMENTS

| | | |
|---|---|---|
| 6,899,849 B2 | 5/2005 | Meinhart et al. |
| 7,586,601 B2 | 9/2009 | Ebstein |
| 8,670,119 B1 | 3/2014 | Bratkovski |
| 2004/0063214 A1 | 4/2004 | Berlin et al. |
| 2006/0061762 A1 | 3/2006 | Dwight et al. |
| 2006/0164634 A1 | 7/2006 | Kamins |
| 2007/0030481 A1 | 2/2007 | Gilbert |

(Continued)

FOREIGN PATENT DOCUMENTS

| | | |
|---|---|---|
| EP | 3440699 A1 | 2/2019 |
| WO | WO-2009088408 A1 | 7/2009 |
| WO | WO-2014021808 A1 | 2/2014 |

OTHER PUBLICATIONS

Choi, C. J. et al. "Single-step Fabrication and Characterization of Photonic Crystal Biosensors with Polymer Microfluidic Channels"; Aug. 8, 2006: http://pubs.rsc.org/en/content/articlelanding/2006/lc/b603514k#!divAbstract.

(Continued)

*Primary Examiner* — Abdullahi Nur
(74) *Attorney, Agent, or Firm* — Rathe Lindenbaum LLP (57) ABSTRACT

A housing may include sidewalls and a base extending between and supported by the sidewalls. The base and the sidewalls form a cavity. The housing support they substrate. The substrate supports a surface enhanced luminescence stage between the substrate and the base.

20 Claims, 4 Drawing Sheets

(56) References Cited

U.S. PATENT DOCUMENTS

| | | |
|---|---|---|
| 2010/0085566 A1 | 4/2010 | Cunningham |
| 2012/0309080 A1 | 12/2012 | Cunningham et al. |
| 2014/0036263 A1* | 2/2014 | Kim .................... G01N 21/658 356/301 |
| 2014/0193892 A1* | 7/2014 | Mohan ................. G01N 21/05 435/287.2 |

OTHER PUBLICATIONS

Fan, M. et al.; "Surface-enhanced Raman scattering (SERS) optrodes for multiplexed on-chip sensing of nile blue A and oxazine 720" Feb. 6, 2012.

Lin, Shiyun, et al. "Surface-enhanced Raman scattering with Ag nanoparticles optically trapped by a photonic crystal cavity." Nano letters 13.2 (2013): 559-563.

Min Hu et al. "Gold nanofingers for Molecule Trapping and Detection", Journal of the American Chemical Society, vol. 132, No. 37, Sep. 22, 2010, pp. 12820-12822.

\* cited by examiner

FIG. 15

SUBSTRATE SUPPORTED SEL STAGE AND HOUSING

BACKGROUND

Surface-enhanced luminescence (SEL) techniques, such as surface-enhanced Raman spectroscopy (SERS), are sometimes used for analyzing the structure of inorganic materials and complex organic molecules. SEL techniques focus electromagnetic radiation or light onto an analyte supported by a stage, wherein the radiation scattered or reflected by the analyte is detected for analysis.

DETAILED DESCRIPTION OF EXAMPLES

Surface-enhanced luminescence (SEL) may be used for analyzing the structure of inorganic materials and complex organic molecules. SEL focuses electromagnetic radiation or light onto an analyte supported by a stage, wherein the radiation scattered or reflected by the analyte is detected for analysis. The stage provides an analyte supporting surface that enhances the analyte response to provide enhanced sensitivity.

The present disclosure describes a simple and low cost SEL stage package. The package comprises a housing that forms a cavity. The housing further supports a substrate that supports the SEL stage. The housing facilitates independent fabrication of the SEL stage upon the substrate, with the substrate and the SEL sensor being simply subsequently mounted in the housing. The housing additionally serves to protect the SEL stage and form a reservoir about the SEL stage for the fluid being tested.

As will be described hereafter, in some implementations, the housing has an architecture that facilitates molding of the housing. The molding may additionally form a focusing lens as well as input and output ports as integral parts of the housing. As a result, the cost and the complexity of the SEL stage package may be further reduced.

Figure 1:
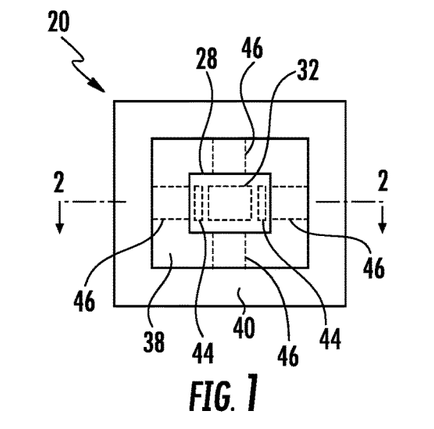
FIG. 1 is a top view schematically of an example SEL stage package.
Figure 2:
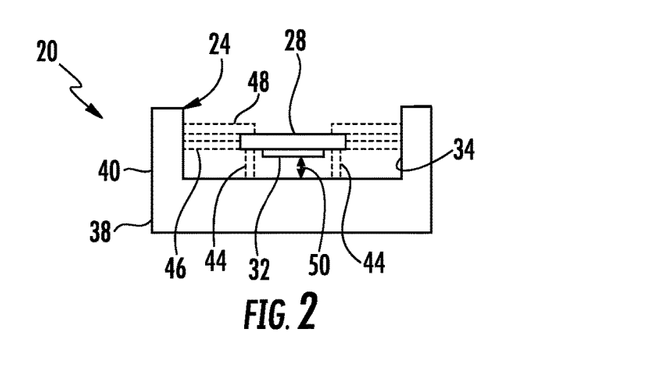
FIG. 2 is a sectional view of the example SEL stage of FIG. 1 taken along line 2-2.

FIGS. 1 and 2 are cross-sectional views schematically illustrating an example SEL stage package 20 for use as part of a SERS sensing system. Package 20 comprises housing 24, substrate 28 and SEL stage 32. Housing 24 surrounds and protects substrate 28 and SEL stage 32. Housing 24 forms a cavity 34 in which substrate 28 and SEL stage 32 are supported. Housing 24 facilitates separate and independent fabrication and/or assembly of substrate 28 and SEL stage 32, wherein substrate 28 and SEL stage 32 may be subsequently mounted or secured in place within cavity 34. Cavity 34 not only surrounds substrate 28 and sensor 32, but may also serve as a reservoir for containing the solution and analyte being tested in contact with SEL stage 32.

Housing 24 comprises base 38 and sidewalls 40. Base 38 extends between and said is supported by sidewalls 40. Base 38 cooperate with sidewalls 40 to form cavity 34. Sidewalls 40 project from base 38 and surround substrate 28 and SEL stage 32. In the example illustrated, sidewalls 40 project from base 38 beyond SEL stage 32. In the example illustrated, sidewalls 40 project from base 38 beyond substrate 28.

In one implementation, sidewalls 40 are bonded, welded or fastened to base 38. In yet another implementation, base 38 and sidewalls 40 are integrally formed as a single unitary homogenous body. For example, in one implementation, base 38 and sidewalls 40 are molded. In another implementation, base 38 and sidewalls 40 are formed through three-dimensional printing. In yet another implementation, the body of housing 24 having a non-final shape distinct from the final shape of housing 24 is formed with molding or 3-D printing, wherein at least portions of the shape are defined by subsequent material removal processes as etching or the like.

In one implementation, at least portions of base 38 generally opposite to SEL stage 32 are formed from a transparent material or materials so as to permit light to be directed through such portions of base 38 onto SEL stage 32. In one implementation, the transparent material forming such portions the base 38 are molded. In one implementation, base 38 is formed from a transparent polymer such as polystyrene, polycarbonate, poly (methyl methacrylate) (PMMA), cyclic olefin copolymer (COC), polydimethylsiloxane (PDMS) or silicone. In yet other implementations, or transparent polymers or other transparent materials may be utilized to form at least portions of base 38. In some implementations, both base 38 and sidewalls 40 are formed from the transparent material.

Substrate 28 comprises a layer or platform supporting SEL stage 32. In one implementation, substrate 28 is formed from a sufficiently flexible material or a group of flexible materials so as to facilitate the fabrication of SEL stage 32 upon substrate 28 in a roll-to roll process. In other implementations, substrate 28 is stiff. In one implementation, substrate 28 may be formed from materials including, but not limited to, COC.

As shown by FIGS. 1 and 2, substrate is supported by housing 24 within cavity 34 while supporting SEL stage 32. In one implementation, substrate 22 may be supported within cavity 34 by columns or posts 44 which extend from base 38 and which are welded, bonded, fastened or otherwise secured to substrate 28. In another implementation, substrate 22 may be supported by support beams 46 that project from the interior sides of sidewalls 40 and which are welded, bonded, fastened or otherwise secured to substrate 28. Although package 20 is illustrated as having a beam 46 on each of the four sides of substrate 28, in other implementations, package 20 may include a single pair of beams 46 on opposite sides of substrate 28. As shown by FIG. 1, in some implementations, substrate 28 may be supported by beams 48 that are secured to a face of substrate 28. For example, FIG. 1 illustrates beams 48 secured to a top face of substrate 28, opposite to the face that supports stage 32. In yet other implementations, substrate 28 may be supported by housing with beams 48 that project from the interior sides of sidewalls 40 and which are welded, bonded, fastened or otherwise secured to the face of substrate 28 from which stage 32 extends.

In one implementation, package 20 may comprise each of post 44 and beams 46 or 48 for supporting substrate 28 in cavity 34 in a plane spaced from the face of base 38 that faces SEL stage 32. In one implementation, post 44, beam 46 and/or beam 48 may be integrally formed with housing 24 as a single unitary body. In yet another implementation, post 44, beam 46 and/or beam 48 may be joined or secured to substrate 28 in a separate assembly process, prior to substrate 28 being mounted to housing 24 within cavity 34. In yet another implementation, post 44, beam 46 and/or beam 48 may be integrally formed with substrate 28 as a single unitary body.

SEL stage 32 comprises a surface enhanced luminescence analyte stage upon which analyte is deposited for testing. For purposes of this disclosure, a surface enhanced luminescence (SEL) analyte stage is any structure or particle that interacts with the deposited analyte so as to enhance the intensity of the radiation scattered or reemitted by the analyte. Stage 32 enhances the amount of radiation or the number of photons that are scattered or re-emitted by the analyte upon being impinged by radiation from a radiation source.

In one implementation, stage 32 comprises an SEL structure or a group of SEL structures supported by substrate 28 upon which and about which an analyte contacts. In one implementation, the SEL structures comprise enhanced fluorescence spectroscopy structures or enhanced luminescence spectroscopy structures. In one implementation, the SEL structures comprise surface enhanced Raman spectroscopy (SERS) structures. Such structures may include a metal surface or structure, wherein interactions between the analyte and the metal surface cause an increase in the intensity of the Raman-scattered radiation. Such metal surfaces may include a roughened metal surface or metal islands. In one implementation, such metal islands comprise columnar supports such as pillars, needles, fingers, particles or wires. In some implementations, the columnar structures may include a metal cap or head upon which analyte may be deposited. In some implementations, such columnar structures are formed from materials and/or are dimensioned so as to bend or flex towards and away from one another in response to applied electric fields. In some implementations, the SEL structures are movable and are self-actuating, wherein such columnar structures bend or flex towards one another in response to micro-capillary forces so as to self-organize, wherein such bending facilitates close spacing between the structures for greater scattered radiation intensity.

In one implementation, the SEL or SER structures have a nanometer scale to facilitate nano-enhanced Raman spectroscopy (NERS). Such nano-scale NERS structures may increase the intensity of radiation scattered by the analyte adsorbed on such structures by a factor as high as $10^{16}$. In other implementations, stage 32 may comprise SEL particles. Examples of SEL particles include, but are not limited to, electrodes in electrolytic cells and metal colloid solutions.

SEL stage 32 is supported by substrate 28 while facing base 38 so as to be sandwiched between substrate 28 and base 38 within cavity 34. In the example illustrated, SEL stage 32 is suspended and spaced from those portions of base 38 that are transparent by a gap 50. The gap between stage 32 and base 38 facilitates focusing of light onto stage 32 through the transparent portions of base 38. In one implementation, the gap has a height or thickness of at least 10 um and no greater than 5 mm. In other implementations, the gap may have other dimensions.

Figure 3:
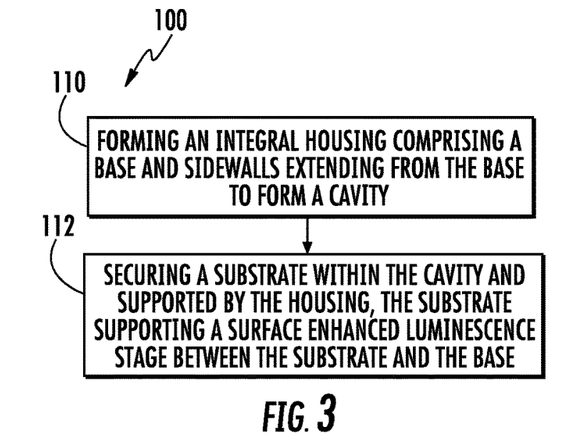
FIG. 3 is a flow diagram of an example method for forming an example SEL stage package.

FIG. 3 is a flow diagram of an example method 100 for forming a SEL package. Method 100 facilitates the fabrication of a SEL package with less complexity and less cost. Although method 100 is described in the context of forming SEL stage package 20, it should be understood that method 100 may be utilized to form any of the SEL stage packages described hereafter.

As indicated by block 110, a housing (such as housing 24) comprising a base 38 and a sidewall 40 extending from the base to form a cavity 34 is integrally formed. For purposes of this disclosure, the term "integrally formed" means that the structure is of a homogenous character with no seams, brakes or junctions between parts of the structure. In one implementation, housing 24 may be integrally formed using a molding process. In one implementation, housing 24 may be integrally formed using a three-dimensional printing process.

As indicated by block 112, a substrate (such a substrate 28) is secured within the cavity 34. The substrate supports a SEL stage. The substrate is mounted within the cavity such that the SEL stage extends between the substrate and the base. In one implementation, the SEL stage is preformed on the substrate prior to the substrate being mounted to the cavity, wherein the substrate, with the SEL stage, is mounted to the housing within the cavity.

Figure 4:
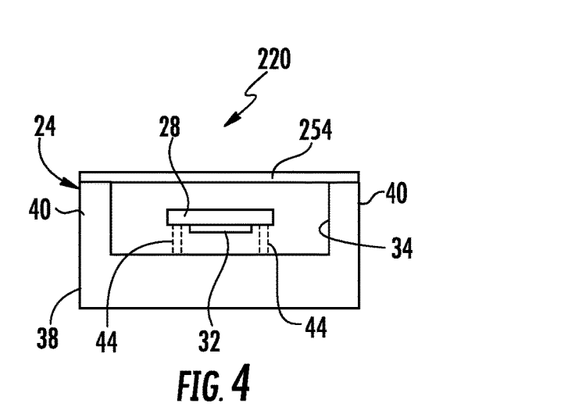
FIG. 4 is a sectional view of an example SEL stage package.

FIG. 4 is a sectional view schematically illustrating an example SEL stage package 220. Package 220 is similar to package 20 described above except that package 220 additionally comprises sealing layer 254 and is specifically illustrated as comprising post 44 supporting substrate 28. Sealing layer 254 comprises a layer of a material or multiple materials that is secured to sidewalls 40 across cavity 34. In one implementation, sealing layer 254 is imperforate and forms an air seal over cavity 34, inhibiting the ingress of air, contaminants or other particles into the cavity 34 and onto stage 32. In some implementations, cavity 34 may be vacuum sealed with layer 254 to inhibit oxidation of particular metals that may be utilized as part of stage 32, such as silver. In one implementation, layer 254 comprises a thin polymeric film, such as a thin film of Aluminum coated polytetrafluoroethylene (PTFE) having a thickness of at least 25 um and no greater than 500 um. In other implementations, layer 254 may be formed from other materials and may have other dimensions.

Figure 5:
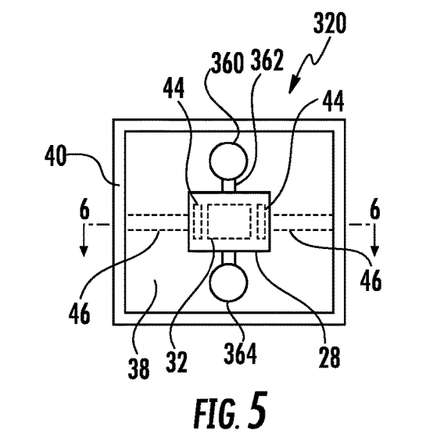
FIG. 5 is a top view an example SEL stage package.
Figure 6:
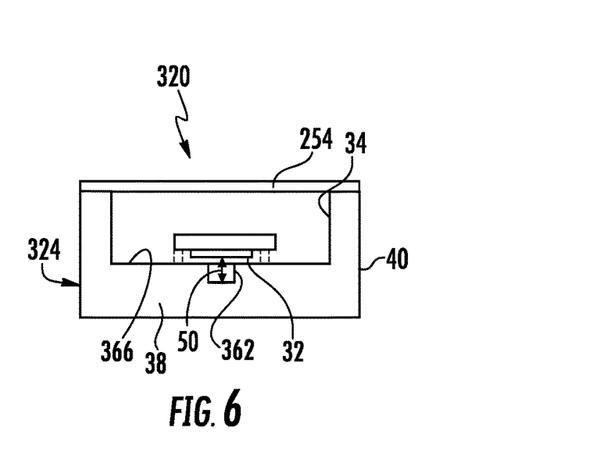
FIG. 6 a sectional view of the example SEL stage package of FIG. 5 taken along line 6-6.

FIGS. 5 and 6 are sectional views illustrating an example SEL stage package 320. Package 320 is similar to package 220 except that package 320 comprises housing 324 in lieu of housing 24. Those remaining components or elements of package 320 which correspond to components or elements of package 220 are numbered similarly. As shown by FIG.

6, in addition to being supported by posts 44, substrate 28 may additionally or alternatively be supported by beams 46 which extend from the interior sides of sidewalls 40. In other implementations, substrate 28 may additionally be supported by beams 48 (described above).

Housing 324 is similar to housing 24 except that housing 324 additionally comprises recesses or channels formed in base 38. In the example illustrated, housing 324 comprises input port 360, flow channel 362 and output port 364. Input port 360, flow channel 362 and output port 364 project into the face 366 of base 38, the floor of cavity 34. Input port 360 forms a basin or well that receives a sample solution. Flow channel 362 facilitates flow of the solution being tested to within the gap 50 between stage 32 and base 38. Output port 364 receives fluid that is passed across stage 32. In one implementation, the channels, such as input port 360, flow channel 362 and output port 364 are created during the integral formation of housing 324, such as during the molding or 3-D printing of housing 324. In other implementations, such channels are formed following the integral formation of housing 324, wherein such channels are formed through material removal processes, such as etching or the like. In one implementation, the formation of such channels occurs prior to the mounting of substrate 28 and stage 32 within cavity 34 and prior to the sealing at cavity 34 by sealing layer 254.

Figure 7:
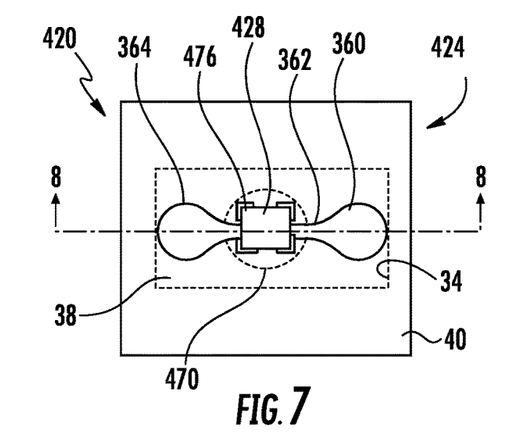
FIG. 7 is a sectional view of an example SEL stage package.
Figure 8:
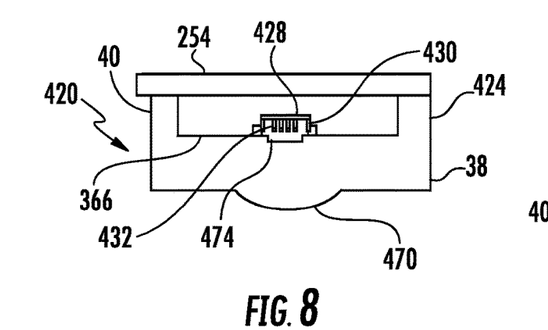
FIG. 8 is a sectional view of the SEL stage package of FIG. 7 taken along line 8-8.

FIGS. 7 and 8 illustrate an example SEL stage package 420. Package 420 comprises housing 424, substrate 428, substrate supports 430, SEL stage 432 and sealing layer 254. Housing 424 is similar to housing 324 described above except that housing 424 additionally comprises focusing lens 470 and recess 474. Those remaining components of housing 424 which correspond to components of housing 324 are numbered similarly.

Focusing lens 470 comprises a transparent material arranged opposite to stage 432 so as to focus or concentrate light rays from an illumination source, such as a laser, onto stage lens. In the example illustrated, lens 432 is supported by base 38, spanning across recess 474. In the example illustrated, lens 470 comprises a dual-sided convex lens, being convex on both sides of base 38 opposite to recess 474 and stage 432. In other implementations, lens 470 may comprise other types of lenses having other focusing characteristics.

In the example illustrated, lens 470 is integrally formed as a single unitary body with base 38. For example, lens 470 is formed during the integral formation of housing 424, being molded with the molding of base 38 or being 3-D printed with base 38. In one implementation, the shape of lens 470 is defined during the molding of base 38 or during the 3-D printing of base 38. In yet another implementation, the body of lens 470 having a non-final shape distinct from the final shape of lens 470 is formed with molding or 3-D printing, wherein at least portions of the shape are defined by subsequent material removal processes as etching or the like. In yet other implementations, lens 470 may be separately formed and may be welded, bonded, fastened or otherwise attached directly to or indirectly to base 38 opposite to recess 474 and stage 432.

In one implementation, those portions of base 38 forming lens 470 are formed from a transparent material or materials so as to permit light to be directed through such portions of base 38 onto SEL stage 432. In one implementation, base 38 is formed from a transparent polymer such as polystyrene, polycarbonate, poly (methyl methacrylate) (PMMA), polydimethylsiloxane (PDMS) or silicone. In yet other implementations, or transparent polymers or other transparent materials may be utilized to form at least portions of base 38. In some implementations, both base 38 and sidewalls 40 are formed from the transparent material.

Recess 474 comprises a depression or cavity formed in surface 366 of base 38 opposite to stage 432 between stage 432 and lens 470. Recess 474 provides additional spacing to the spacing provided by gap 50 between lens 470 and stage 432. The additional spacing facilitates focusing of light by focusing lens onto stage 432. Recess 474 further assists in guiding and holding a retaining the analyte being tested opposite to stage 432. In one implementation, the gap 50 and the depth of recess 474 have a collective height or thickness of at least 10 um and no greater than 5 mm. In other implementations, the collective height may have other dimensions.

Substrate 428 comprises a layer or platform supporting SEL stage 432. In one implementation, substrate 428 is formed from a sufficiently flexible material or a group of flexible materials so as to facilitate the fabrication of SEL stage 432 upon substrate 428 in a roll-to roll process. In other implementations, substrate 428 is stiff. In one implementation, substrate 28 may be formed from materials including, but not limited to, COC.

Substrate supports 430 comprise columns or posts 44 which extend from base 38 and which are welded, bonded, fastened or otherwise secured to substrate 428. In another implementation, substrate 428 may be supported by support beams 46 that project from the interior sides of sidewalls 40 and which are welded, bonded, fastened or otherwise secured to substrate 428. As shown by FIG. 1, in some implementations, substrate 428 may be supported by supports 430 that are secured to a face of substrate 428. In one implementation, substrate supports 430 are formed from SU8. In other implementations, substrate supports 430 may be formed from other materials such as UV curable Epoxy.

SEL stage 432 comprises surface enhanced Raman spectroscopy (SEL) structures. In the example illustrated, stage 432 comprises pillars, needles, fingers, nano rods or wires. In some implementations, the columnar structures may include a metal cap or head upon which analyte may be deposited. In some implementations, such columnar structures are formed from materials and/or are dimensioned so as to bend or flex towards and away from one another in response to applied electric fields. In some implementations, the SEL structures are movable and are self-actuating, wherein such columnar structures bend or flex towards one another in response to micro-capillary forces so as to self-organize, wherein such bending facilitates close spacing between the structures for greater scattered radiation intensity.

In one implementation, the SEL or SER structures have a nanometer scale to facilitate nano-enhanced Raman spectroscopy (NERS). Such nano-scale NERS structures may increase the intensity of radiation scattered by the analyte adsorbed on such structures by a factor as high as $10^{16}$. In other implementations, stage 432 may comprise other SERS or other SEL structures.

SEL stage 432 is supported by substrate 428 while facing base 38 so as to be sandwiched between substrate 428 and base 38 within cavity 34. In the example illustrated, SEL stage 32 is suspended and spaced from those portions of base 38 that are transparent by a gap 50. The gap between stage 32 and base 38 facilitates focusing of light onto stage 32 through the transparent portions of base 38. In one implementation, the gap has a height or thickness of at least 10 um and no greater than 5 mm. In other implementations, the gap may have other dimensions.

Figure 9A:
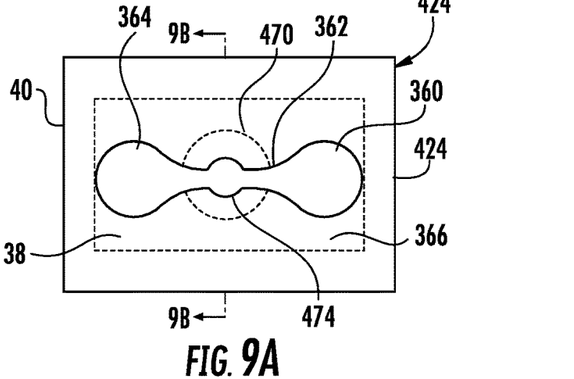
FIG. 9A is a top view of an example SEL stage package housing.
Figure 9B:
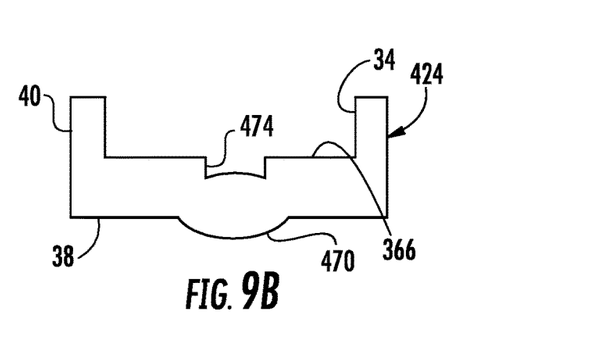
FIG. 9B is a sectional view of the SEL stage package housing of FIG. 9A take along line 9B-9B.

FIGS. 9A-12B illustrate one example method of forming package 420. FIGS. 9A and 9B illustrate housing 424. As described above, in the example illustrated, housing 424 comprises a single integral unitary body which comprises each of base 38, sidewalls 40, inlet port 360, channel 362, outlet port 364, focusing lens 470 and recess 474. As described above, housing 424 is integrally formed through a process such as molding or 3-D printing. In one implementation, the final shapes of each of such structures are defined during such molding or 3-D printing. In other implementations, the final shapes of such structures are defined by the tour removal processes following such molding or 3-D printing.

Figure 10A:
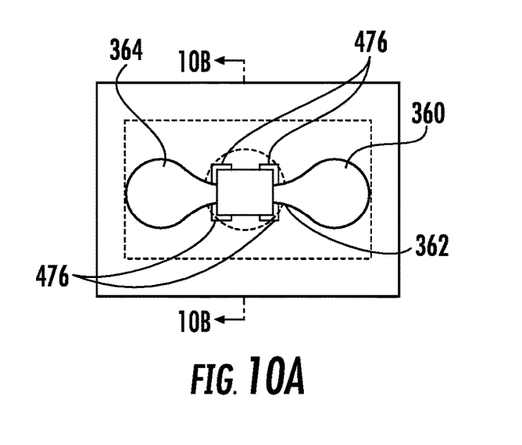
FIG. 10A is a top view of the example SEL stage package housing of FIG. 9A with an applied adhesive layer.
Figure 10B:
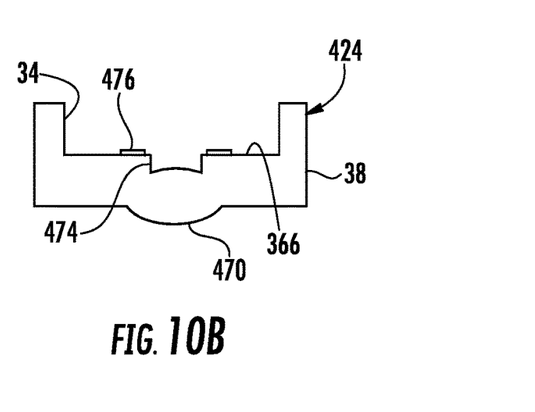
FIG. 10B is a sectional view of the SEL stage package housing of FIG. 10A take along line 10B-10B.

As shown by FIGS. 10A and 10B, housing 424 is prepared for securement of stage 432 by adding or depositing a layer 476 of adhesive on surface 366 of base 38 about recess 474. In one implementation, the adhesive layer 476 comprises a layer of adhesive material such as EMS405-57 Epoxy. In other implementations, the application of visa may be omitted where other mechanisms are employed for securing stage 432 to housing 424, such as welding of the like.

Figure 11A:
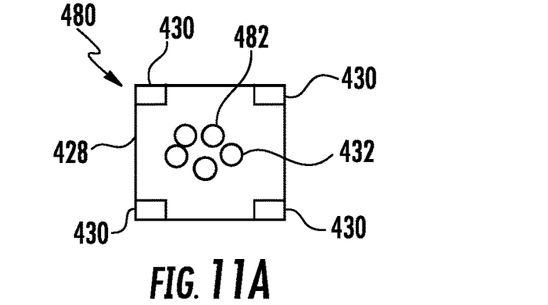
FIG. 11A is a top view of an example stage module.
Figure 11B:
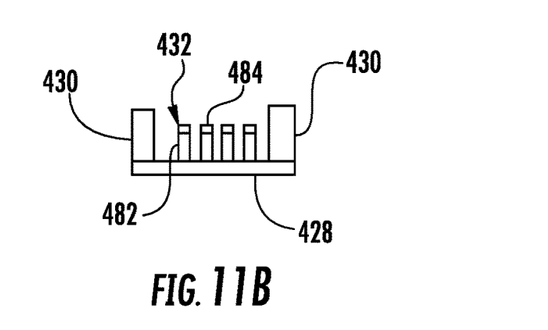
FIG. 11B is a sectional view of the stage module of FIG. 11A.

FIGS. 11A and 11B illustrates one example stage module 480 that is formed independent of housing 424 and prior to securement within cavity 34 of housing 424. Module 480 comprises a package or unit of interconnected components that it itself may be then mounted to housing 424 as part of the process for assembling package 420. In the example illustrated, module 480 comprises substrate 428, supports 430 and stage 432.

As shown by FIGS. 11A and 11B, substrate 428 serves as a platform upon which supports 430 are formed or secured. In the example illustrated, supports 430 comprise for posts or mesas extending from each corner of substrate 428 about stage 432. Each support extends beyond the tops of each of the nano-fingers of stage 432. In one implementation, supports 430 and the nano fingers of stage 432 are concurrently formed. For example, in one implementation, supports 430 and the nano fingers of stage 432 are concurrently formed by imprinting a layer of material, such as an epoxy based photoresist, such as SU8 (a Bisphenol A Novolac epoxy that is dissolved in an organic solvent), supported by substrate 428, wherein metal tips are subsequently formed on the ends of the nano fingers.

Although illustrated as being rectangular columns, posts 430 may have other shapes. Although illustrated as comprising four equally spaced supports 430, in other implementations, module 480 may comprise other numbers and/or other layouts or arraignments of supports 430. In other implementations, module 480 may omit supports 430, such as where supports 430 are secured to surface 366 of base 38 of housing 424 prior to the mounting of module 480 to housing 424. In some implementations, housing 424 may additionally comprise substrate supports 430 which are also integrally formed as part of a single unitary body as part of housing 424.

As further shown by FIGS. 11A and 11B, in the example illustrated, stage 432 comprises a cluster of five individual nano rods 482, wherein the individual nano rods 42 bend in directions towards one another to enhance Raman spectroscopy plasmonic response. As specifically shown by FIG. 11B, each of the individual nano fingers 482 has a metallic tip 484, such as a metallic tip of gold, silver or the like, to further enhance Raman spectroscopy plasmonic response. In one implementation, each nano finger 482 has a height or length rejecting from substrate 428 of at least 0.05 um and no greater than 50 um. In one implementation, each of nano fingers 42 are spaced from one another by at least 0.2 um and no greater than 10 um. In yet other implementations, stage 432 may comprise a greater or fewer of such individual nano fingers 482 arranged in a cluster, multiple clusters, a single grid or other arrangements. In other implementations, nano fingers 42 may have other configurations or may omit tips 44.

Figure 12A:
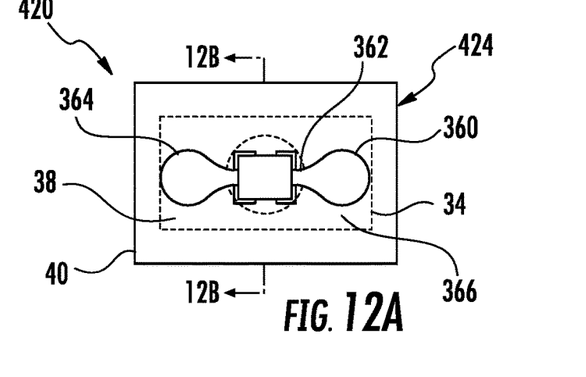
FIG. 12A is a top view of the example stage module of FIG. 11A inverted and mounted within the example housing of FIG. 10A.
Figure 12B:
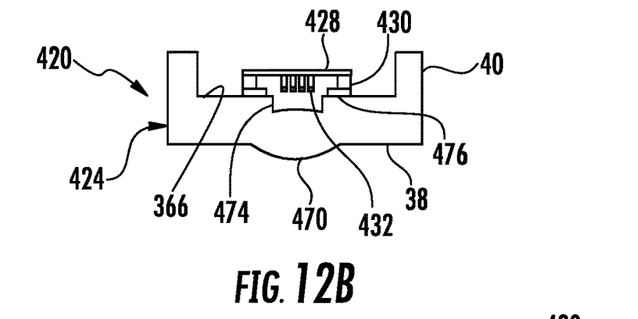
FIG. 12B is a sectional view of the example stage module an example housing of FIG. 12A taken along line 12B-12B.

As shown by FIGS. 12A and 12B, module 480 is flipped and mounted upon the adhesive pads formed by adhesive layer 476. The adhesive layer 476 secures supports 430 to surface 366 of base 38 with the nano fingers 482 of stage 432 being suspended of the above recess 474 opposite to focusing lens 470. Thereafter, as shown by FIG. 8, sealing layer 254, which completely covers cavity 34, is secured to sidewalls 40 over cavity 34 and over module 480. In one implementation, ceiling layer 254 is peelable or removable from sidewalls 40. In another implementation, sealing layer 254 is puncturable or tearable, allowing the solution or liquid being tested to be injected or deposited into cavity 34.

Figure 13:
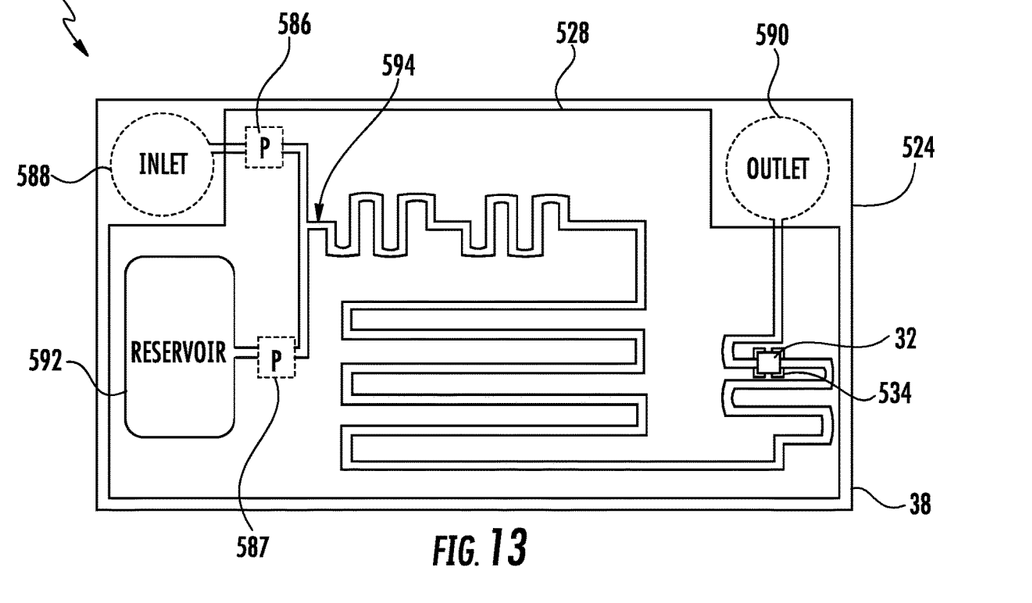
FIG. 13 is a top view of an example SEL package.

FIG. 13 is a top view of an example SEL stage package 520. Package 520 is similar to package 420 except that package 520 comprises housing 524, substrate 528 and fluid pumps 586, 587. Similar to package 420, package 520 comprises stage 32 which is supported by substrate 528 within cavity 34 within housing 524 opposite to a focusing lens 470 (shown in FIG. 12B) which is provided on the underside of housing 524. In one implementation, the focusing lens 470 is integrally formed as a single unitary body as part of housing 524 similar to shown in FIG. 12B. In other implementations, focusing lens 470 may be attached to an underside of housing 524 or may be omitted.

Housing 524 forms a cavity 534 opposite to stage 32. In one implementation, unlike housing 424, the sidewalls of the cavity 534 comprise sidewalls of the cavity formed within surface 366 of base 38. Substrate 528 overlies and contacts surface 366 over and above such sidewalls of the cavity 534 while suspending stage 32 opposite to cavity 534. In such an implementation, supports 430 may be omitted.

In addition to cavity 34 described above, housing 524 comprises multiple cavities or channels. In the example illustrated, housing 524 comprises inlet cavity 588, outlet cavity 590, reservoir cavity 592 and flow channels 594. Inlet cavity 588 comprises a recess formed in the lower face of base 38 of housing 524, the same face of which is provided a focusing lens 470. Inlet cavity provides a port through which a solution being tested is deposited.

Outlet cavity 590 comprises a recess formed in the lower face of base 38 of housing 524, the same face of which is provided a focusing lens 470. Outlet cavity provides a port through which a solution being tested is discharged.

Reservoir cavity 592 comprises a recess formed in the upper face of base 38 of housing 524, the same face into which cavity 534 extends. Reservoir cavity 592 provides a chamber in which an additional solution to be mixed with the solution deposited in inlet cavity 588, such as reagent, is stored.

Flow channels 594 comprise grooves formed in the upper face of base 38 of housing 524 that interconnect cavities 588, 590 and 594. Flow channels 594 are further connected to cavity 34. Flow channel 594 facilitates mixing of the solutions or liquids provided in inlet cavity 588 and reservoir cavity 590. Flow channel 594 further delivers the solution to stage 32, prior to the solution being delivered to outlet cavity 590. In some implementations, flow channel 594 may further deliver the solutions to or across other functional stations between inlet cavity 588 and outlet cavity 590 for performing other operations on the solution, such as filtering and the like.

Substrate 528 is similar to substrate 428 described above in that substrate 528 supports stage 32. In the example illustrated, substrate 528 additionally provides a top or cap over reservoir cavity 592, flow channels 594 and cavity 34. Similar to substrate 428, substrate 528 may be formed from a sufficiently flexible material or a group of flexible materials so as to facilitate the fabrication of SEL stage 32 upon substrate 528 in a roll-to roll process. In other implementations, substrate 528 is stiff. In one implementation, substrate 528 may be formed from materials including, but not limited to, COC.

Fluid pumps 586 and 587 comprise devices to pump or move fluid along flow channels 594. Examples of pumps 586, 587 include, but are not limited to, a piezoelectric membrane, a thermal bubble resistor pump, and electrostatic micro-electro-mechanical system (MEMS) membrane, a mechanical/impact driven membrane, a voice coil pump and a magneto-strictive drive pump. In one implementation, each of pump 586, 587 may comprise an inertial pump, wherein the pump 586, 587 is asymmetrically located along the length of a channel, spaced from ends of the channel by different distances, such that the pump 586, 587 propagates oppositely directed waves and produces a unidirectional net fluid flow in a selected direction. In one implementation, pumps 586, 587 are carried or suspended by substrate 528. In another implementation, pumps 586, 587 formed or mounted to the floors of cavities formed within housing 524. In yet another implementation, as described below, pumps 586, 587 may be suspended from substrate 528 in a cavity formed within housing 524.

Figure 14:
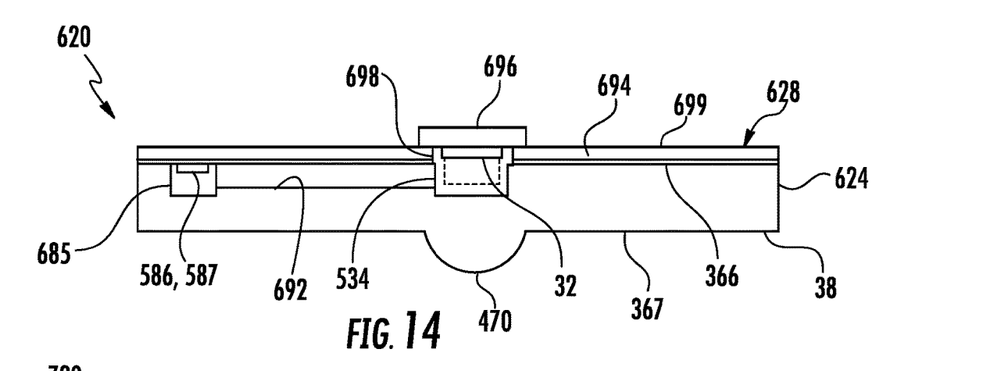
FIG. 14 is a sectional view of an example SEL package.

FIG. 14 is a sectional view of a portion of an example SEL package 620. FIG. 14 illustrates one example of how stage 32 (schematically shown) and pumps 586 and/or 587 may be supported by an example substrate 628 with respect to an example housing 624. Housing 624 is similar to housing 524 in that housing 624 comprises (A) a cavity 534 extending into face 366 of base 38 of housing 624 and positioned opposite to an integral focusing lens 470; (B) a cavity 685 extending into face 366 of base 38 of housing 624 and positioned opposite to one of pumps 586, 587; and (C) at least one flow channel 692 extending between and interconnecting cavity 534 and cavity 685.

In one implementation, cavity 534, cavity 685 and flow channel 692 are each formed in face 366 of housing 624. In one implementation, cavity 534, cavity 685 and flow channel 692 are molded or 3-D printed as part of housing 624. In another implementation, cavity 534, cavity 685 and flow channel 692 are formed through material removal processes, such as etching. Although not illustrated, in one implementation, housing 624 additionally comprises inlet cavity 588 and outlet cavity 590 (shown and described with respect to FIG. 13) which are formed in lower face 367 of housing 624 and which are connected by flow channel 692. In some implementations, housing 624 additionally comprises reservoir channel 592 described above with respect to FIG. 13.

Substrate 628 is similar to substrate 528 described above except that substrate 628 comprises a lower portion 694 and an upper portion 696. Lower portion 694 is directly secured to face 366 of base 38 of substrate 624. Lower portion 694 includes a window or opening 698 at least partially aligned with cavity 534 and focusing lens 470. Opening 698 is sized larger than the size of stage 32 such that opening 698 receives stage 32. Lower portion 694 serves as a side wall supporting and spacing upper portion 696 above cavity 534. Lower portion 694 further spans and covers flow channel 692 as well as a reservoir cavity 590 (shown in FIG. 13).

In the example illustrated, lower portion 694 further supports one of pumps 586, 587 opposite to and within cavity 685. In one implementation, pumps 586, 587 may be formed upon lower portion 694 of substrate 628, independent of the fabrication of housing 624, wherein lower portion 694 in the supported pump 586, 587 are laminated to or otherwise secured to face 366 of housing 624 with pump 586, 587 and positioned within cavity 685. In one implementation, lower portion 694 of substrate 628 is sufficiently flexible such that lower portion 694 and pump 586, 587, such as a bubble jet resistor, maybe formed as part of a roll-to roll process.

Upper portion 696 is similar to substrate 428. Upper portion 696 support stage 32 while covering opening 698. Upper portion 696 support stage 32 within window 698. In some implementations, as indicated by broken lines, lower portion 694 and stage 32 may be dimensioned such as stage 32 projects into cavity 534 opposite to focusing window 470.

In one implementation, upper portion 696 is sufficiently flexible such that of a portion 696 and stage 32 may be formed as part of a roll-to roll process. In one implementation, upper portion 696 may be formed as an elongate strip supporting a series of spaced stages 32, wherein the individual spaced stages are suddenly separated and wherein of upper portion 696 is mounted otherwise secured to face 699 of lower portion 694 with stage 32 being received within opening 698 opposite to cavity 534 and focusing lens 470. In other implementations, a proportion 696 and stage 32 may be part of a larger wafer containing a two dimensional array of stages 32 on a sheet of the material of upper portion 696, wherein the two dimensional array of stages 32 are severed or separated to form multiple individual units, each unit comprising an upper portion 696 and a stage 32.

Figure 15:
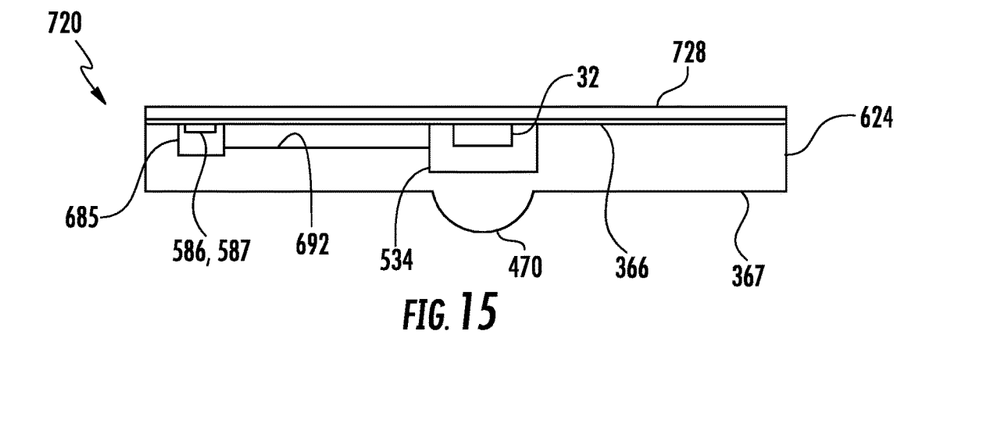
FIG. 15 is a sectional view of an example SEL package.

FIG. 15 is a sectional view of an example SEL package 720. Package 720 is similar to package 620 except that package 720 comprises substrate 728 in view of substrate 628. Those remaining components of package 720 which correspond to components of package 620 are numbered similarly.

Substrate 728 is similar to substrate 528 in that substrate 728 covers and expands across each of cavity 534, cavity 685 and flow channel 692. As with substrate 628, substrate 728 supports at least one of pumps 586, 587 within cavity 685. In one implementation, pumps 586, 587 may be formed upon lower portion 694 of substrate 728, independent of the fabrication of housing 624, wherein lower portion 694 in the supported pump 586, 587 are laminated to or otherwise secured to face 366 of housing 624 with pump 586 or pump 587 positioned within cavity 685.

As further shown by FIG. 15, substrate 728 further supports stage 32 (schematically shown). In the example illustrated, stage 32 and pump 586/587 are formed upon substrate 728 at spaced positions such that substrate 728 may be inverted with pump 586/587 and stage 32 being concurrently aligned with and received within cavity 685 and 534, respectively. In one implementation, substrate 728 may be formed as an elongate strip supporting a series of spaced stages 32, wherein the individual spaced stages are subsequently separated and wherein substrate 728 is mounted or otherwise secured to face 366 of housing 624 with stage 32 being received within opening 698 opposite to cavity 534 and focusing lens 470 and with pump 586/587 received within cavity 685. In other implementations, a substrate 728, pump 586/587 and stage 32 may be part of a larger wafer containing a two dimensional array of package clusters, each package cluster comprising at least one stage 32 and at least one pump 586, 587 for an individual SEL package, wherein the two dimensional array of package clusters are severed or separated to form multiple individual package clusters. Each package cluster may then be laminated or adhered to face 366 of housing 624 to complete the SEL package.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. An apparatus comprising:
   a housing comprising:
      sidewalls; and
      a base extending between and supported by the sidewalls, the base and the sidewalls forming a cavity;
   a substrate supported by the housing; and
   a surface enhanced luminescence (SEL) stage supported by the substrate between the substrate and the base, wherein the base comprises a focusing lens opposite the SEL stage.

2. The apparatus of claim 1, wherein the substrate is supported by the housing within the cavity.

3. The apparatus of claim 1, wherein the focusing lens and the base are formed as a single integral unitary body.

4. The apparatus of claim 1, wherein the focusing lens, the base and the sidewalls are formed as a single integral unitary body.

5. The apparatus of claim 1 further comprising a recess extending from the cavity into a face of the base opposite the focusing lens, between the base and the SEL stage.

6. The apparatus of claim 1, wherein the housing further comprises:
   an input port through one of the sidewalls and the base; and
   an output port through one of the sidewalls and the base.

7. The apparatus of claim 1 further comprising a sealing layer secured to the sidewalls across the cavity.

8. The apparatus of claim 1, wherein the SEL stage comprises nano fingers projecting from the substrate towards the base, each of the nano fingers having a metallic tip.

9. The apparatus of claim 1, wherein the lens comprises a dual sided convex lens located to focus light onto the SEL stage.

10. The apparatus of claim 1, wherein the base forms a floor of the cavity and wherein the base further comprises a recess projecting into the floor and towards the lens opposite the SEL stage.

11. The apparatus of claim 1 further comprising:
   an input port projecting into a face of the base;
   an output port projecting into the face of the base; and
   a flow channel projecting into the face of the base, the flow channel extending between the input port and the output port.

12. The apparatus of claim 11 further comprising a fluid pump supported by one of the substrate and the base.

13. The apparatus of claim 12, wherein the fluid pump is supported by the substrate opposite the base.

14. The apparatus of claim 1, wherein the housing comprises a first panel having a recess forming the sidewalls, the base and the cavity and wherein the substrate comprises a second panel facing into joined to the first panel with the SEL stage opposite the cavity.

15. A method comprising:
   molding a housing comprising:
      sidewalls; and
      a base extending between and supported by the sidewalls over an underlying cavity; and
   securing a substrate supported to the housing opposite the cavity, the substrate supporting a surface enhanced luminescence (SEL) stage between the substrate and the base, wherein the base comprises a focusing lens opposite the SEL stage.

16. The method of claim 15, wherein securing the substrate to the housing comprises suspending the substrate from the base within the cavity.

17. The method of claim 15, wherein the focusing lens and the base are formed as a single integral unitary body.

18. The method of claim 15, wherein the focusing lens, the base and the sidewalls are formed as a single integral unitary body.

19. The method of claim 15, wherein the housing further comprises:
   an input port through one of the sidewalls and the base; and
   an output port through one of the sidewalls and the base.

20. An apparatus comprising:
   a single integrated unitary body forming a housing comprising:
      sidewalls; and
      a base extending between and supported by the sidewalls over an underlying cavity, the base comprising a lens;
   a substrate supported by the housing; and
   a surface enhanced Raman luminescence (SEL) stage supported by the substrate between the substrate and the base, opposite the lens.

* * * * *